US00PP19262P3

(12) United States Plant Patent
Layt

(10) Patent No.: US PP19,262 P3
(45) Date of Patent: Sep. 23, 2008

(54) *LOMANDRA LONGIFOLIA* PLANT NAMED 'KATRINUS DELUXE'

(50) Latin Name: *Lomandra longifolia*
Varietal Denomination: Katrinus Deluxe

(76) Inventor: Todd Anthony Layt, P.O. Box 1011, Richmond, NSW (AU), 2753

( * ) Notice: Subject to any disclaimer, the term of this patent is extended or adjusted under 35 U.S.C. 154(b) by 0 days.

(21) Appl. No.: 11/904,798

(22) Filed: Sep. 28, 2007

(65) Prior Publication Data

US 2008/0127393 P1 May 29, 2008

Related U.S. Application Data

(60) Provisional application No. 60/848,313, filed on Sep. 29, 2006.

(51) Int. Cl.
*A01H 5/00* (2006.01)

(52) U.S. Cl. ..... Plt./384

(58) Field of Classification Search ..... Plt./384
See application file for complete search history.

*Primary Examiner*—Annette H Para
*Assistant Examiner*—S. B. McCormick-Ewoldt

(57) ABSTRACT

'Katrinus Deluxe' is a distinctive variety of *Lomandra longifolia* which is characterized by the combination of its dense plant growth habit, medium-tall plant height, narrow-medium leaf width, large inflorescence size and presence of male flowers only.

1 Drawing Sheet

Latin name of the genus and species: The Latin name of the genus and species of the novel variety disclosed herein is *Lomandra longifolia.*

Variety denomination: The inventive variety of *Lomandra* disclosed herein has been given the variety denomination 'Katrinus Deluxe'.

BACKGROUND OF THE INVENTION

The present invention relates to a new and distinct perennial variety of *Lomandra longifolia,* which has been given the variety denomination of 'Katrinus Deluxe'. Its market class is that of an ornamental grass-like plant. 'Katrinus Deluxe' is intended for use in landscaping and as a decorative grass-like plant.

The *Lomandra longifolia* variety 'Katrinus Deluxe' was first discovered in 1999 in an Australian nursery in the state of New South Wales during a routine inspection of large quantities of *Lomandra longifolia* 'Katrinus' (unpatented) production stock. 'Katrinus Deluxe' is a seedling selection of open pollinated *Lomandra longifolia* 'Katrinus'. 'Katrinus Deluxe' was selected due to its dense plant growth habit, narrower leaf width, large inflorescence size and presence of male flowers only. 'Katrinus Deluxe' was first propagated asexually by division in the state of New South Wales, Australia and has since been asexually propagated by division and micropropagation. The distinctive characteristics of the inventive 'Katrinus Deluxe' variety are stable from generation to generation; clones of the variety produced by asexual reproduction maintain the distinguishing characteristics of the original plant.

'Katrinus Deluxe' has a dense growth habit with leaves that are finer and more narrow than *Lomandra longifolia* 'Katrinus' (unpatented in the United States; Australian Plant Breeders' Rights Application No. 1997/168), 'Cassica' (unpatented in the United States: Australian Plant Breeders' Rights Application No. 1997/166) and common *Lomandra longifolia.*

An application for plant breeders' rights for variety 'Katrinus Deluxe' has been lodged with the Australian Plant Breeders' Rights Office, and was received in October 2005 under Application No. 2005/316.

SUMMARY OF THE INVENTION

'Katrinus Deluxe' is a distinctive variety of *Lomandra longifolia* which is characterized by the combination of its dense plant growth habit, medium-tall plant height, narrow-medium leaf width, large inflorescence size and presence of male flowers only.

BOTANICAL DESCRIPTION OF THE PLANT

Figure 1:
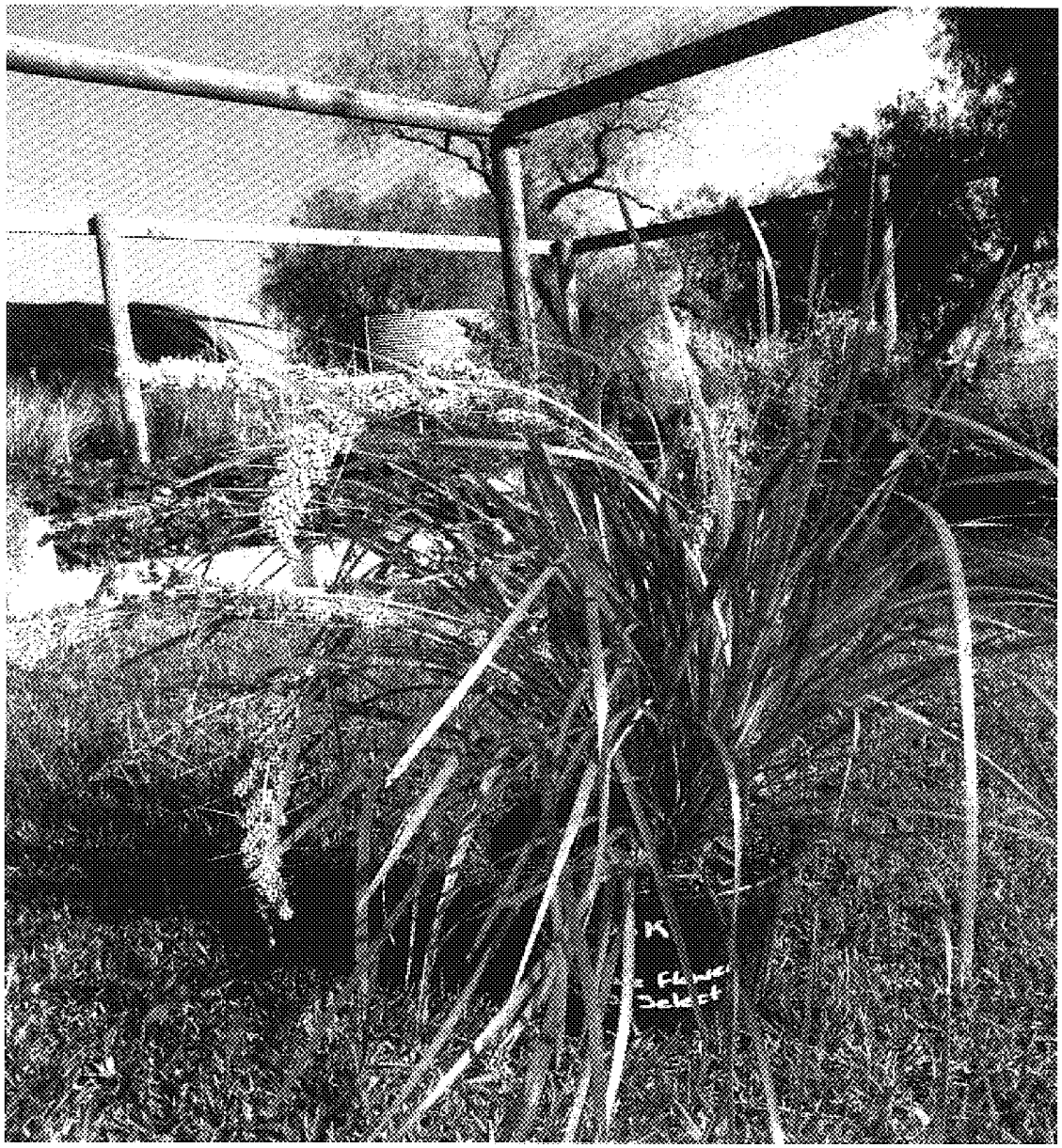
FIG. 1 shows a 'Katrinus Deluxe' plant.

The following is a detailed botanical description of a new and distinct variety of a *Lomandra longifolia* ornamental grass-like plant known as 'Katrinus Deluxe'. Plant observations were made on plants grown in New South Wales, Australia. Unless indicated otherwise, the descriptions disclosed herein are based upon observations made in September 2005 of mature 'Katrinus Deluxe' plants grown in nursery pots and field plots.

Those skilled in the art will appreciate that certain characteristics will vary with older, or conversely, younger plants. 'Katrinus Deluxe' has not been observed under all possible environmental conditions. Where dimensions, sizes, colors and other characteristics are given, it is to be understood that such characteristics are approximations or averages set forth as accurately as practicable. The phenotype of the variety may vary with variations in the environment such as season, temperature, light intensity, day length, cultural conditions and the like. Color notations are based on The Royal Horticultural Society Colour Chart, The Royal Horticultural Society, London, 1995 edition. 'Katrinus Deluxe' is undergoing further trialing and comparative testing in Australia and the United States.

'Katrinus Deluxe' is a perennial *Lomandra longifolia* plant which originated from a seedling selected from a population of open pollinated plants of *Lomandra longifolia* 'Katrinus'. After its selection, 'Katrinus Deluxe' was asexually propagated by division and subsequently by micropropagation. 'Katrinus Deluxe' has a narrow-medium leaf blade width combined with a densely shooted plant growth habit, which is unusual for *Lomandra longifolia* plants which usually have a broader leaf blade and a lower density of shoots per tussock.

Growth Habit, Dimensions and Color: 'Katrinus Deluxe' is a medium-tall, rhizomatous plant forming a dense tussock. Average plant height is 110 cm and average plant spread is 100 cm in a mature plant grown in a 300 mm nursery or field pot in Sydney, New South Wales, Australia. The upper and lower side of the leaf is yellow green (circa RHS 137C) in color. The leaf blade is generally 5 to 8 mm in width, and 90 cm in length. The leaf base is cauline, leaf margin is entire, leaf apex is tridentate and leaf surface glaucosity is weak. The leaf venation pattern is parallel; the color is the same as the rest of the leaf (yellow-green RHS 137C; observed spring 2005). The basal shoots are grayed orange (circa RHS 166A-B) in color (observed spring 2005). The leaf is generally a uniform width from base to the tip, margins may shred at the base, with a tridentate apex typical of *Lomandra longifolia.* A representative 'Katrinus Deluxe' plant is shown in FIG. 1.

Roots: Similar to other *Lomandra longifolia,* 'Katrinus Deluxe' has a massive root structure. The roots are fibrous and spreading, similar to other *Lomandra longifolia.*

Rhizomes: Short (3 cm to 4 cm); rhizome color with the leaf sheath removed is white (RHS 155C); surface texture of the rhizome is smooth.

Bud: Bud shape is oval. Bud color is greyed purple (RHS 183C); observed spring 2005.

Inflorescence: The inflorescence is a spike (a panicle of clusters), composed of male flowers. The predominant color of the inflorescence at anthesis is yellow (RHS 6A; observed spring 2005).

Floret Length: The average length of the floret is 3.3 mm (observed spring 2005).

Pedicels: Absent; the florets are sessile.

Bracts: Average bract length is 30 mm; bract color is grayed orange (approximately RHS 164D). Observations made in spring 2005.

Flowers: Color of outer perianth is greyed purple (RHS 183C) proximally, yellow green (RHS 146A-B) distally along the central zone, and greyed yellow (RHS 161D) along each perianth segment margin; color of inner perianth is yellow (RHS 6A) fading toward the margin to yellow (RHS 13D). Observations made spring 2005.

Flower Rachis: The length of the flower rachis is 150–170 mm (observed spring 2005).

Reproductive Organs of Male Florets: Six stamens, anther size is 0.5 mm to 0.8 mm in length, anther color is yellow (approximately RHS 8B), observed spring 2005.

Seed: Flowers are male; seed is not produced.

Flowering Period: The primary flowering period is in the spring with secondary flowering occurring in summer to autumn in Sydney, New South Wales, Australia.

Lastingness of Bloom: Approximately 9 days in summer flowering in Sydney, New South Wales, Australia.

Fragrance: Fragrance is typical of the species.

Comparison of 'Katrinus Deluxe' with Other Varieties of *Lomandra longifolia*

The leaf blade width of 'Katrinus Deluxe' is narrower than that of 'Katrinus', 'Cassica' and the common form of *Lomandra longifolia.*

'Katrinus Deluxe' has a more dense plant growth habit than 'Katrinus'. 'Katrinus Deluxe' has a similar plant height than 'Katrinus', is taller than 'Cassica' and slightly shorter than the common form of *Lomandra longifolia.* The combination of its dense plant growth habit and narrow leaf makes 'Katrinus Deluxe' an attractive ornamental grass-like plant.

'Katrinus Deluxe' has a significantly larger flower spike than 'Katrinus' and the common form of *Lomandra longifolia.* 'Katrinus Deluxe' only produces male flowers and does not produce viable seed whilst 'Katrinus' and the parent type of *Lomandra longifolia* typically produce viable seed in female plants.

The flower spike of 'Katrinus Deluxe' is relatively spiky to touch, similar to 'Katrinus' and the parent type of *Lomandra longifolia.* The novelty and distinctiveness of 'Katrinus Deluxe' as compared with other varieties of *Lomandra longifolia* is still undergoing further testing.

Asexual Reproduction: After its initial discovery, 'Katrinus Deluxe' was transplanted into a 140 mm pot for further trials and testing. After divisions were made for several subsequent generations, 'Katrinus Deluxe' was observed to retain plant growth characteristics that were noted in the original 'Katrinus Deluxe' seedling. 'Katrinus Deluxe' was then divided into many larger pots for further evaluation and introduction to micropropagation.

Environmental Tolerances: 'Katrinus Deluxe' has shown potential for shade tolerance and further shade tolerance tests are underway. The winter hardiness of 'Katrinus Deluxe' is at least to zone 8*a* in the Southeastern United States, and evaluation of winter hardiness is ongoing. 'Katrinus Deluxe' has been observed to hold color to −10 degrees Celsius without any noticeable change in appearance of the plant. 'Katrinus Deluxe' has excellent drought tolerance. After severe wilting. 'Katrinus Deluxe' has been noted to recover with watering. 'Katrinus Deluxe' does well in sandy soils, but also tolerates heavy, clay-type soils well.

Disease Resistance: 'Katrinus Deluxe' has good resistance to root rot compared with most other *Lomandra longifolia* and evaluation of disease resistance is ongoing.

That which is claimed is:

1. A new and distinct variety of *Lomandra longifolia* plant named 'Katrinus Deluxe', substantially as described and illustrated herein.

* * * * *